(12) United States Patent
Behler et al.

(10) Patent No.: US 7,268,259 B1
(45) Date of Patent: Sep. 11, 2007

(54) RANDOM FATTY ALCOHOL ALKOXYLATES WITH LOW TEMPERATURE STABILITY, AND METHODS OF PRODUCING AND USING THE SAME

(75) Inventors: Ansgar Behler, Bottrop (DE); Horst-Dieter Schares, Erkrath (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/486,677

(22) PCT Filed: Aug. 24, 1998

(86) PCT No.: PCT/EP98/05355

§ 371 (c)(1),
(2), (4) Date: Jun. 26, 2000

(87) PCT Pub. No.: WO99/11593

PCT Pub. Date: Mar. 11, 1999

(30) Foreign Application Priority Data

Sep. 1, 1997 (DE) ................... 197 38 108

(51) Int. Cl.
*C07C 43/04* (2006.01)
*C11D 1/722* (2006.01)

(52) U.S. Cl. ............. 568/618; 568/625; 510/506; 43/124; 43/132.1; 252/351

(58) Field of Classification Search ........ 568/618, 568/625; 252/351; 510/506; 43/124, 132.1
See application file for complete search history.

(56) References Cited

U.S. PATENT DOCUMENTS

| | | | |
|---|---|---|---|
| 3,382,285 A | 5/1968 | Egan et al. | 260/615 |
| 3,770,701 A | 11/1973 | Cenker et al. | 260/658 |
| 4,093,418 A | 6/1978 | Compton et al. | 8/142 |
| 4,280,919 A | 7/1981 | Stoeckigt et al. | 252/135 |
| 4,731,378 A * | 3/1988 | Naik et al. | 514/531 |
| 4,999,041 A * | 3/1991 | Grossmann et al. | 504/162 |
| 5,516,451 A * | 5/1996 | Schmitt et al. | 516/129 |

FOREIGN PATENT DOCUMENTS

| | | |
|---|---|---|
| EP | 0 019 173 A1 | 11/1980 |
| EP | 0 086 493 A1 | 8/1983 |
| GB | 1172931 A | 12/1969 |
| JP | 07-303825 A | 11/1995 |

\* cited by examiner

*Primary Examiner*—Rosalynd Keys
(74) *Attorney, Agent, or Firm*—John F. Daniels; Jane E. Keene

(57) ABSTRACT

Random fatty alcohol alkoxylates with low temperature stability which are polymerization products of fatty alcohols, ethylene oxide and propylene oxide, according to the general formula (I):

$$R^1O[(EO)_n(PO)_m]-H \qquad (I)$$

wherein $R^1$ represents an alkyl group having from about 6 to about 22 carbon atoms, each EO represents —$CH_2CH_2O$—, each PO independently represents —$C(CH_3)HCH_2O$— or —$CH_2C(CH_3)HO$—, wherein n represents the average number of EO units present in each random fatty alcohol alkoxylate and has a value of from about 2 to about 7, and wherein m represents the average number of PO units present in each random fatty alcohol alkoxylate and has a value of from about 1.5 to about 3; are disclosed. A process for the production of such random fatty alcohol alkoxylates and methods of their use in water-dilutable concentrates are also disclosed.

15 Claims, No Drawings

RANDOM FATTY ALCOHOL ALKOXYLATES WITH LOW TEMPERATURE STABILITY, AND METHODS OF PRODUCING AND USING THE SAME

BACKGROUND OF THE INVENTION

Alcohol alkoxylates, which are also known as alkyl polyglycol ethers, are compounds which have been known for decades and which are obtained by reacting alcohols with ethylene oxide and/or propylene oxide. The reaction takes place at elevated temperatures and pressures in the presence of acidic or alkaline catalysts. The use of basic compounds of the alkali and alkaline earth metals is of particular practical significance for the alkoxylation of fatty alcohols. Suitable basic compounds are alkali metal and alkaline earth metal alkoxylates, such as sodium methylate and potassium methylate, or alkali metal and alkaline earth metal hydroxides, such as sodium hydroxide and potassium hydroxide. Recently, alkali metal and alkaline earth metal hydroxides have preferably been used as basic catalysts because, where alkali metal and alkaline earth metal alkoxylates are used, organic solvents, such as methanol, are essential. By contrast, where the alkali metal and alkaline earth metal hydroxides are used, the reaction gives good yields, even in aqueous medium.

However, where aqueous solutions of alkali metal and alkaline earth metal hydroxides are used as basic catalysts, products with unfavorable low-temperature behavior which often tend to precipitate, even at room temperature, are obtained, particularly in the ethoxylation of the fatty alcohols. This is attributable inter alia to the fact that the presence of aqueous solutions of alkali metal and alkaline earth metal hydroxides promotes the formation of high molecular weight polyethylene glycols as secondary products. Although, in principle, these polyethylene glycols can be removed by extraction with suitable solvents, such as water, this does involve another process step which is very time-consuming and, in addition, cannot be universally applied.

According to the abstract of Japanese patent application 07,303,825 from the Journal CA Selects in: Alkoxylated Oleochemicals, Issue 1996, page 5, published by the American Chemical Society, Columbus, Ohio, No. 124, random adducts of $C_{8-18}$ alcohols containing 5 to 15 moles of ethylene oxide and 0.3 to 5.0 moles of propylene oxide show improved flow behavior at low temperatures. In the only example cited, lauryl alcohol is reacted with about 9 moles of ethylene oxide and about 2.4 moles of propylene oxide in the presence of potassium hydroxide as basic catalyst, a product with a pour point of 7.5° C. being obtained. However, this product also tends to precipitate in storage at temperatures below 0° C. which is problematical.

The problem addressed by the present invention was to provide fatty alcohol alkoxylates which would show very favorable low-temperature behavior and would not have any tendency to precipitate. The low-temperature behavior would be so pronounced that the products would remain clear liquids even at temperatures below 0° C. so that no precipitation would occur, even in the event of storage at low temperatures. In addition, the products obtained would be readily soluble in cold water so that they would, be suitable for use as surface-active compounds, for example in liquid concentrates of detergents. In addition, the compounds would lend themselves to production in the presence of aqueous solutions of bases.

BRIEF SUMMARY OF THE INVENTION

The problem stated above has surprisingly been solved by random polymers of fatty alcohols which contain ethylene oxide and propylene oxide in random-polymerized form in a certain selected ratio.

The present invention includes low-temperature stable random polymers of fatty alcohols with ethylene oxide and propylene oxide, the ethylene oxide and propylene oxide being present in a certain selected quantity ratio. The present invention also includes a process for the production of such random polymers of fatty alcohols, and to methods of using such polymers as surfactants in water-dilutable concentrates including, for example, concentrates of detergents, pesticides and/or agrochemicals.

Accordingly, the present invention relates to random polymers of fatty alcohols with ethylene oxide and propylene oxide corresponding to formula (I):

$$R^1O(EO)_n(PO)_mH \qquad (I)$$

in which $R^1$ is an alkyl group containing 6 to 22 carbon atoms, EO stands $CH_2CH_2O$, PO stands for $CHCH_3CH_2O$ and/or $CH_2CHCH_3O$, n is a whole or broken number of 2 to 7 and m is a whole or broken number of 1.5 to 3, characterized in that the molar ratio of propylene oxide to ethylene oxide is from 10:90 to 50:50.

Random polymers of fatty alcohols corresponding to formula (I), in which the molar ratio of propylene oxide to ethylene oxide is from 25:75 to 40:60, are particularly preferred.

In addition, random polymers of fatty alcohols corresponding to formula (I), in which n is a whole or broken number of 3 to 5, and random polymers of formula (I), in which m is a whole or broken number of 2 to 2.5, are preferred.

DETAILED DESCRIPTION OF THE INVENTION $R^1$ in formula (I) is derived from fatty alcohols with the formula $R^1OH$ which contain 6 to 22 carbon atoms. Fatty alcohols in this context are understood to be primary aliphatic alcohols in which $R^1$ is an aliphatic, linear or branched hydrocarbon radical containing 6 to 22 carbon atoms and 0 and/or 1, 2 or 3 double bonds. Typical examples are caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or aldehydes from Roelen's oxosynthesis and as monomer fraction in the dimerization of unsaturated fatty alcohols.

According to the invention, technical fatty alcohols containing at least 30% by weight $C_{14-18}$ fatty alcohols and at most 70% by weight $C_{6-12}$ fatty alcohols are preferred. The percentages by weight are based on the fatty alcohol mixture. Examples of such fatty alcohol mixtures are coconut, palm, palm kernel or tallow fatty alcohol.

The random polymers according to the invention are distinguished by very good low-temperature behavior, i.e. they are free-flowing and preferably clear even at temperatures below 0° C. The low-temperature behavior is determined by measurement of the cold cloud point in accordance with DIN ISO 3015. The products according to the invention are also distinguished by very good solubility in cold water, i.e. they have very short dissolving times. Dissolving behavior was determined by measuring the time which 10 g of the compound takes to form an optically clear solution in 90 g of stirred deionized water (temperature 23° C.).

The present invention also relates to a process for the production of random polymers of fatty alcohols corresponding to formula (I) by reacting ethylene oxide and propylene oxide with fatty alcohols corresponding to the formula $R^1OH$ in the presence of aqueous bases, characterized in that propylene oxide and ethylene oxide in a molar ratio of 10:90 to 40:60 are reacted with fatty alcohols in known manner.

The random polymerization is a process known per se in which the above-described alcohols $R^1OH$ are reacted with propylene and ethylene oxide in a pressure vessel at temperatures of 120 to 190° C. under a pressure of 3 to 5 bar. According to the invention, aqueous solutions of alkali metal and/or alkaline earth metal hydroxides, for example potassium hydroxide, are used as the basic compounds. The hydroxides are normally used in quantities of 0.2 to 5% by weight and preferably in quantities of 0.3 to 1.5% by weight, expressed as hydroxide and based on the mixture as a whole. It is advisable to use the hydroxides in the form of 40 to 60% by weight aqueous solutions. Propylene and ethylene oxide are reacted together with the fatty alcohols. To this end, they may be separately introduced into the reaction vessel through two different nozzles or may even be premixed in a mixing vessel and then introduced into the reactor. It is crucial to the invention that propylene oxide and ethylene oxide are used in the quantities and mixing ratios mentioned above. In general, ethylene oxide is used in a quantity of 2 to 7 moles and preferably 3 to 5 moles per mole fatty alcohol while propylene oxide is used in a quantity of 1.5 to 3 moles and preferably 2 to 2.5 moles per mole of fatty alcohol. A molar mixing ratio of propylene oxide to ethylene oxide of preferably 25:75 to 40:60 is of particular significance. The reaction of ethylene oxide and propylene oxide together with the fatty alcohols gives so-called random polymers, i.e. the addition takes place in statistical distribution.

If desired, the process according to the invention may be followed by neutralization of the basic catalyst. The neutralization step may be carried out with inorganic and/or organic acids, such as lactic acid, oxalic acid, citric acid, acetic acid, phosphoric acid or methane sulfonic acid. Neutralization to values of 6.5 to 7.5 is generally advisable when unsaturated fatty alcohols are used because they easily discolor under the influence of atmospheric oxygen. The products are obtained in the form of a 100% clear liquid.

The present invention also relates to the use of the above-described random polymers of fatty alcohols as surface-active agents in water-dilutable concentrates, for example in concentrates of detergents or in concentrates of pesticides and agrochemicals. In recent years, detergents, for example, have been increasingly marketed as concentrates which contain only a little water. Such concentrates can be diluted with water before use by the end user. The concentrates are expected to dissolve quickly without forming any precipitates. This is achieved by using the compounds according to the invention as surface-active agent. The products according to the invention may be used in detergent concentrates in quantities of 10 to 30% by weight, based on active ingredient in the concentrate. The concentrates may additionally contain typical constituents, such as anionic surfactants, nonionic surfactants, preservatives, solubilizers, etc., which are typical of detergents, in the usual quantities.

The products according to the invention may be used in pesticide and agrochemical concentrates in quantities of 0.1 to 15% by weight, based on active principle in the concentrate. In this case, too, the concentrates may contain typical constituents in typical quantities.

EXAMPLES

1. Production of a Random Polymer of a $C_{12/14}$ alcohol+ 5EO+2PO 366.3 g (1.89 moles) of a $C_{12}/C_{14}$ fatty alcohol mixture (about 40% $C_{12}$ and 60% by weight $C_{14}$) were introduced into a pressure vessel with 5 g of a 50% by weight aqueous potassium hydroxide solution. The vessel was then evacuated for 30 minutes at 100° C. and subsequently purged with nitrogen. A mixture of 414.9 g (9.43 moles) of ethylene oxide and 218.8 g (3.77 moles) of propylene oxide was then introduced at 120° C. The maximum pressure was 5 bar. On completion of the reaction, the mixture was stirred for 1 hour at 120° C. and the reactor evacuated for another 30 minutes at 120° C. The product obtained was neutralized with lactic acid.

A clear liquid product with a cold cloud point of −4° C. was obtained; the dissolving time in water was 5 seconds.

2. Production of a Random Polymer of a $C_{12/14}$ alcohol+ 3EO+2PO

As in Example 1, 439.1 g (2.26 moles) of a $C_{12}/C_{14}$ fatty alcohol were reacted with a mixture of 298.5 g (6.78 moles) of ethylene oxide and 262.4 g (4.52 moles) of propylene oxide in the presence of 5 g of a 50% by weight aqueous potassium hydroxide solution.

A clear liquid product with a cold cloud point of −14° C. which took 3 seconds to dissolve in water was obtained.

Comparison Example 1

Block Polymer of a $C_{12/14}$ Alcohol with 1 PO+5EO+1 PO

In accordance with Example 1, the quantities of fatty alcohol described in Example 1 were reacted first at 120° C. with 109.4 g (1.89 moles) of propylene oxide, then at 180° C. with 414.9 g (9.43 moles) of ethylene oxide and, on completion of the reaction, at 120° C. with another 109.4 g (1.89 moles) of propylene oxide.

A clear liquid product with a cold cloud point of 1.5° C. was obtained. The dissolving time in water was 75 seconds.

Comparison Example 2

Block Polymer of a $C_{12/14}$ alcohol with 5EO+2PO

In accordance with Example 1, the quantity of fatty alcohol described in Example 1 was reacted first at 180° C. with 414.9 g (9.43 moles) of ethylene oxide and then at 120° C. with 218.8 g (3.77 moles) of propylene oxide.

A clear liquid product with a cold cloud point of 7.5° C. was obtained. The dissolving time in water was 8 seconds.

What is claimed is:

1. A mixture of polymers comprising random fatty alcohol alkoxylates according to the general formula (I):

$$R^1O[(EO)_n(PO)_m]-H \tag{I}$$

wherein $R^1$ represents an alkyl group having from about 6 to about 22 carbon atoms, each EO represents —$CH_2CH_2O$—, each PO independently represents —$C(CH_3)HCH_2O$— or —$CH_2C(CH_3)HO$—, and wherein n represents the average number of EO units present in each random fatty alcohol alkoxylate and has a value of from about 3 to about 5, and wherein m represents the average number of PO units present in each random fatty alcohol alkoxylate and has a value of from about 2 to about 2.5, wherein the mixture exhibits a cold cloud point below 0° C.

2. The mixture according to claim 1, wherein $R^1O$ represents a fatty alcohol residue derived from a fatty alcohol mixture, said mixture comprising at least about 30% by weight of alcohols having from about 14 to about 18 carbon atoms and up to about 70% by weight of alcohols having from about 6 to about 12 carbon atoms.

3. A process for producing a mixture of polymers comprising random fatty alcohol alkoxylates according to the general formula (I);

 (I)

wherein $R^1$ represents an alkyl group having from about 6 to about 22 carbon atoms, each EO represents —$CH_2CH_2O$—, each PO independently represents —$C(CH_3)HClH_2O$— or —$CH_2C(CH_3)HO$—, and wherein n represents the average number of EO units present in each random fatty alcohol alkoxylate and has a value of from about 3 to about 5, and wherein m represents the average number of PO units present in each random fatty alcohol alkoxylate and has a value of from about 2 to about 2.5; said process comprising reacting ethylene oxide, propylene oxide and fatty alcohol in the presence of an aqueous base, wherein the propylene oxide and the ethylene oxide are present during the reaction In a molar ratio of from about 10:90 to about 60:40, and wherein the mixture exhibits a cold cloud point below 0° C.

4. The process according to claim 3, wherein the propylene oxide and the ethylene oxide are present during the reaction in a molar ratio of from about 10:90 to about 50:50.

5. The process according to claim 3, wherein the propylene oxide and the ethylene oxide are present during the reaction in a molar ratio of from about 25:75 to about 50:50.

6. The process according to claim 3, wherein the propylene oxide and the ethylene oxide are present during the reaction in a molar ratio of from about 25:75 to about 40:60.

7. The process according to claim 3, wherein said fatty alcohol is a mixture of at least two fatty alcohols, said mixture comprising at least about 30% by weight of alcohols having from about 14 to about 18 carbon atoms and up to about 70% by weight of alcohols having from about 6 to about 12 carbon atoms.

8. The process according to claim 3, wherein said aqueous base comprises a hydroxide selected from the group consisting of alkali metal hydroxides and alkali earth metal hydroxides.

9. The process according to claim 8, wherein said hydroxide comprises potassium hydroxide.

10. The product of the process according to claim 3.

11. A water-dilutable concentrate comprising an active ingredient and a surfactant, said surfactant comprising a mixture of polymers comprising random fatty alcohol alkoxylates according to the general formula (I):

 (I)

wherein $R^1$ represents an alkyl group having from about 6 to about 22 carbon atoms, each EO represents —$CH_2CH_2O$—, each PO independently represents —$C(CH_3)HCH_2O$— or —$CH_2C(CH_3)HO$—, wherein n represents the average number of EO units present in each random fatty alcohol alkoxylate and has a value of from about 3 to about 5, and wherein m represents the average number of PO units present in each random fatty alcohol alkoxylate and has a value of from about 2 to about 2.5, wherein the mixture exhibits a cold cloud point below 0° C.

12. The water-dilutable concentrate according to claim 11, wherein said active ingredient comprises one or more components selected from the group consisting of detergents, agrochemicals and pesticides.

13. The water-dilutable concentrate according to claim 11, wherein said active ingredient comprises a detergent, and wherein said surfactant is present in an amount of from about 10% to about 30% by weight, based on the active ingredient.

14. The water-dilutable concentrate according to claim 11, wherein said active ingredient comprises an agrochemical and/or a pesticide, and wherein said surfactant is present in an amount of from about 0.1% to about 15% by weight based on the active ingredient.

15. The water-dilutable concentrate according to claim 11, wherein $R^1O$ represents a fatty alcohol residue derived from a fatty alcohol mixture, said mixture comprising at least about 30% by weight of alcohols having from about 14 to about 18 carbon atoms and up to about 70% by weight of alcohols having from about 6 to about 12 carbon atoms.

* * * * *